United States Patent [19]

Knifton et al.

[11] Patent Number: 4,469,895

[45] Date of Patent: Sep. 4, 1984

[54] PROCESS FOR PREPARING ALCOHOLS FROM OLEFINS AND SYNTHESIS GAS

[75] Inventors: John F. Knifton, Austin; Robert A. Grigsby, Jr., Georgetown, both of Tex.

[73] Assignee: Texaco Inc., White Plains, N.Y.

[21] Appl. No.: 435,814

[22] Filed: Oct. 21, 1982

[51] Int. Cl.³ .............................................. C07C 45/50
[52] U.S. Cl. .................................... 568/454; 568/909; 568/882
[58] Field of Search ........................ 568/454, 882, 909

[56] References Cited

U.S. PATENT DOCUMENTS

| | | | |
|---|---|---|---|
| 3,239,566 | 3/1966 | Slaugh et al. | 568/454 |
| 3,527,809 | 9/1970 | Pruett | 568/454 |
| 3,636,159 | 1/1972 | Solomon | 568/454 |
| 4,306,084 | 12/1981 | Pettit | 568/454 |
| 4,306,085 | 12/1981 | Kim et al. | 568/454 |
| 4,317,936 | 3/1982 | Kim et al. | 568/454 |
| 4,390,729 | 6/1983 | Oswald | 568/454 |

FOREIGN PATENT DOCUMENTS

| | | | |
|---|---|---|---|
| 751353 | 12/1970 | Belgium | 568/454 |
| 988943 | 7/1961 | United Kingdom | 568/454 |
| 966461 | 8/1964 | United Kingdom | |
| 999461 | 7/1965 | United Kingdom | 568/454 |
| 1138601 | 1/1969 | United Kingdom | 568/454 |

OTHER PUBLICATIONS

Pruett, "Advances in Organometallic Chemistry", vol. 17, Catalysis and Organic Synthesis, pp. 1–57 (1979) Academic Press, N.Y.
Pittman et al., "J. Organic Chem.", vol. 46, pp. 1901.
Sanchez-Delgado et al., "Journal of the Chemical Society", Dalton Trans. 1 (1976), pp. 399–404.

*Primary Examiner*—Werren B. Lone
*Attorney, Agent, or Firm*—Jack H. Park; Richard A. Morgan; Cynthia L. Kendrick

[57] ABSTRACT

This invention concerns an improved process of preparing predominantly linear alcohols which comprises the steps of contacting a mixture of terminal and/or internal olefins and synthesis gas with a catalyst system comprising a ruthenium-containing compound in conjunction with one or more tertiary amine promoters, dispersed in a low melting quaternary phosphonium salt and heating said resultant reaction mixture under a pressure of 100 psi or greater at a temperature of at least 50° C. for a sufficient time to produce said alcohols.

24 Claims, No Drawings

PROCESS FOR PREPARING ALCOHOLS FROM OLEFINS AND SYNTHESIS GAS

BACKGROUND OF THE INVENTION

1. Field of the Invention

This invention concerns an improved process for preparing predominantly linear alcohols by the reaction of synthesis gas and terminal or internal olefins in the presence of a catalyst system.

2. Prior Art

The processes of hydroformylation and carbonylation are well known in the art and involve reactions represented by:

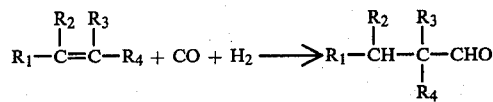

and/or

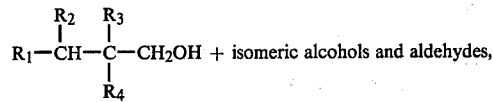

wherein the aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with consequent variation in the products obtained.

The hydroformylation reaction does not generally proceed in the absence of catalysts, and a disadvantage of many of the hydroformylation processes disclosed heretofore is their dependence upon the use of catalysts, particularly the commonly used cobalt-derived homogenous 'oxo' catalysts, which generally necessitate the use of exceedingly high pressures to remain stable under the conditions employed. A further disadvantage of many of the processes disclosed heretofore is their inability to produce hydroformylation products comprising substantial amounts of alcohols, thereby necessitating a separate aldehyde hydrogenation step when alcohols are a desired product. The production of hydroformylation products having a relatively high normal to branched product isomer ratio is also often exceedingly difficult, if at all possible, in many of the practical scale processes now in use. Another problem in many commonly practiced hydroformylation processes is by-product formation on account of competing reactions. Examples of such unwanted by-products include alkanes, formed through competing olefin hydrogenation, olefin isomers formed through double bond isomerization, ketone formation and aldols generated as a result of product aldehyde condensation reactions.

In commercially practiced hydroformylation processes cobalt- and rhodium-catalyzed systems are most commonly used[1], while cobalt and rhodium have been the focus of much of the prior hydroformylation research, numerous other metals have been disclosed as catalysts for this synthesis.

[1] For a review of the prior art pertaining to the use of cobalt and rhodium-based hydroformylation processes see: R. L. Pruett, "Advances in Organometallic Chemistry", Vol. 17, page 1 (1979).

Typical of the prior art relating to the use of ruthenium as a hydroformylation catalyst are the publications of Wilkinson and co-workers. In British Pat. No. 1,138,601, Example 6, the hydroformylation of the alpha-olefins (1-hexene) to aldehydes is described using soluble, phosphine-stabilized ruthenium catalyst precursors, such as $[(Ph_2EtP)_6Ru_2Cl_2]Cl$. Here moderately high pressures are used and the use of a two step hydroformylation and subsequent hydrogenation step as a synthetic route to alcohols is discussed. Additional information regarding the use of a variety of tertiary-phosphine-ruthenium complexes in the catalytic hydroformylation of alkenes to aldehydes-particularly the dependence of conversion and aldehyde ratios upon catalyst concentration, temperature, partial and total pressures, nature of the substrate, and the addition of excess phosphine may be found in a second publication by this group in J. Chem. Soc., page 399 (1976). Similar classes of catalysts are disclosed also in U.S. Pat. No. 3,239,566, assigned to Shell Oil Company. In particular, this patent relates to the production of aldehydes and/or alcohols by the addition of carbon monoxide and hydrogen olefinic hydrocarbons in the presence of a catalyst consisting of a ruthenium or rhodium component in complex combination with carbon monoxide and a trialkylphosphine. Here, the greatest percentage of the converted olefins form alcohols and aldehydes with less than seven carbons.

The use of ruthenium salts, such as ruthenium(III) chloride and ruthenium stearate, as well as ruthenium carbonyls and ruthenium on carbon, as catalyst precursors for the hydroformylation of olefins to straight-chain and branched aldehydes is disclosed in British Pat. Nos. 966,461 and 999,461, assigned to Imperial Chemical Industries Limited. Pettit, in U.S. Pat. No. 4,306,084, describes an oxo process reaction where the ruthenium carbonyl catalyst is maintained in a basic solution. Recently the cluster anion, $[HRu_3(CO)_{11}]^-$, has been shown to catalyze the hydroformylation of ethylene and propylene to $C_3$–$C_4$ aldehydes in dimethylformamide at 100° C. (see C. Suss-Fink, J. Organomet. Chem., 193, C20 (1980)).

Polymer-bound ruthenium hydroformylation catalysts, prepared for example by reacting diphenylphosphinated styrene-divinylbenzene resins with phosphine-stabilized ruthenium carbonyls, have also been described recently. Pittman, in J. Org. Chem. 46, 1901 (1981), finds improved normal/branched aldehyde ratios with these resins compared with homogenous catalyst versions. The more desirable alcohol products are not reported to be formed with this class of ruthenium catalyst.

U.S. Pat. No. 3,239,569 discloses the production of aldehydes and alcohols in a single stage conversion which comprises contacting an olefinic hydrocarbon with carbon monoxide and hydrogen in the presence of a catalyst system comprising cobalt in complex combination with carbon monoxide and a trialkylphosphine. Here again, the majority of the hydroformylation products were six carbons or less.

There is then a need in the art for a one stage process for preparing alcohols from olefinically unsaturated compounds by a process which utilizes lower pressures and results in a high yield of predominantly linear alcohols of the $C_3$–$C_{20}$ range.

An object of this invention, therefore, is to oxonate terminal and/or internal olefins, but particularly higher molecular weight, $C_7$–$C_{14}$ linear alpha olefins fractions, at pressures lower than previously used, to produce predominantly aliphatic $C_8$–$C_{15}$ range alcohols and to outline a method of recovering the product alcohol from the non-volatile, ruthenium-containing, amine promoted catalyst.

The advantages of this process include a yield with a high percentage of linearity of surfactant grade alcohols and intermediate aldehydes; ease of processing, because in many previous systems where cobalt is present one must "de-cobalt" the system; and, the feature of the low volatility of the system compared to a cobalt system.

SUMMARY OF THE INVENTION

This invention concerns a method of making predominantly linear alcohols which comprises the steps of contacting a mixture of CO and $H_2$ and terminal or internal olefins with a catalyst system composed of a ruthenium-containing compound in conjunction with a tertiary amine promoter dispersed in a low melting quaternary phosphonium salt and heating said resultant reaction mixture under a pressure of 100 psi or greater at a temperature of at least 50° C. for a sufficient time to produce said alcohols.

DETAILED DESCRIPTION OF THE INVENTION

In the narrower and more preferred practice of this invention, predominantly linear alcohols are prepared from a synthesis gas mixture of carbon monoxide and hydrogen and olefin substrates by a process comprising the following steps:

(a) Contacting said mixture of carbon monoxide, hydrogen and terminal and/or internal olefin with a catalyst system comprising a ruthenium-containing compound in conjunction with a bidentate or multidentate tertiary amine promoter dispersed in a low melting quaternary phosphonium salt of an organic or mineral acid.

(b) Heating said reaction mixture to a temperature of between 100° and 220° C., at a pressure of 500 psi or greater, and (c) Isolating said alcohols contained therein.

In order to present the inventive concept in the greatest possible detail to promote its understanding, the following supplementary disclosure is submitted. The basic invention, improved upon here is practiced as follows:

Catalysts that are suitable in the practice of this invention contain ruthenium. The ruthenium-containing catalyst may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise ruthenium in complex combination with carbon monoxide, hydrogen and possibly the olefin substrates. The most effective catalyst is believed to be achieved where a ruthenium hydrocarbonyl species in conjunction with an N-heterocyclic amine promoter is solubilized in a quaternary phosphonium salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium (III) triiodide, tricarbonylruthenium (II) iodide, anhydrous ruthenium(III) chloride and ruthenium nitrate, or as the salt of a suitable organic carboxylic acid, for example, ruthenium(III) acetate, ruthenium naphthenate, and ruthenium valerate. Ruthenium(III) acetylacetonate is also a suitable catalyst precursor for this process. The ruthenium may furthermore be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of a mineral acid, ruthenium salts of an organic carboxylic acid and ruthenium carbonyl or hydrocarbonyl derivatives. Among the particularly preferred are ruthenium(IV) oxide, ruthenium(III) acetylacetonate, and triruthenium dodecacarbonyl. The usefulness of these ruthenium precursors for alcohol and aldehyde synthesis is illustrated by the accompanying Examples.

The ruthenium-containing compound is, prior to its catalytic use in making alcohols, first dispersed in a low melting quaternary phosphonium salt.

The quaternary phosphonium salt must be relatively low melting, that is, melt at a temperature less than about the temperature of reaction of making alcohols and aldehydes. Usually the quaternary compound has a melting point less than about 180° C., and most often has a melting point less than 150° C.

Suitable quaternary phosphonium salts have the formula:

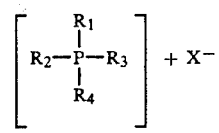

where $R_1$, $R_2$, $R_3$ and $R_4$ are organic radicals, particularly alkyl, aryl or alkaryl radicals bonded to the phosphorous atom, and X is an anionic species. The organic radicals particularly useful in this instance include those alkyl radicals having 1 to 20 carbon atoms in a branched or linear alkyl chain; they include the methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance.

Equally useful are the phosphonium salts containing phosphorus bonded to a mixture of alkyl, aryl and alkaryl radicals. Said aryl and alkaryl radicals may each contain 6 to 20 carbon atoms. The aryl radical is most commonly phenyl. The alkaryl group may comprise phenyl substituted with one or more $C_1$–$C_{10}$ alkyl substituents, bonded to the phosphorus atom through the aryl function.

Illustrative examples of suitable quaternary phosphonium salts include tetrabutylphosphonium bromide, hexadecyltributylphosphonium bromide, heptyltriphenylphosphonium bromide, tetrabutylphosphonium iodide, tetrabutylphosphonium chloride, tetrabutylphosphonium nitrate, tetrabutylphosphonium chromate, tetrabutylphosphonium tetrafluoroborate, tetrabutylphosphonium acetate. The accompanying examples provide evidence of the effectiveness of these quaternary phosphonium salts when in combination with ruthenium(IV) oxide, triruthenium dodecacarbonyl and ruthenium (III) acetylacetonate.

Mixed alkyl phosphonium quaternary salts containing two or more different alkyl groups are also useful in the practice of this invention. A mixed alkyl phosphonium salt by which good results are obtained in the practice of this invention is hexadecyltributylphosphonium bromide.

The preferred quaternary salts are generally the tetralkylphosphonium salts containing alkyl groups having 1-6 carbon atoms, such as methyl, ethyl, and butyl. Preferred tetrabutylphosphonium salts include the bromide, chloride, iodide, acetate and chromate salts. Tetrabutylphosphonium salts, such as tetrabutylphosphonium bromide, are most preferred for the practice of this invention.

The addition of the quaternary phosphonium salts to the ruthenium-containing compounds described SUPRA generally ensures the following improvements in olefin hydroformylation performance.
(1) Improved yields of desired alcohol plus aldehyde product.
(2) Less by-product hydrocarbon formation.
(3) Ease of separation of the ruthenium catalyst from the alcohol and aldehyde products.
(4) Maintained activity for the ruthenium catalyst during multiple recycling experiments.

Illustrative of these improvements are the accompanying Examples, particularly Example XLV and comparative Examples XLVI and XLVIII, as well as Example XLII and comparative Examples XLIII and XLIV.

Amine promoters are generally added to the ruthenium catalyst in the practice of this invention for the purpose of improving the product alcohol and aldehyde linearity (i.e., the ratio of straight-chain aliphatic alcohol product (A), to branched chain alcohol product, illustrated here by structure B).

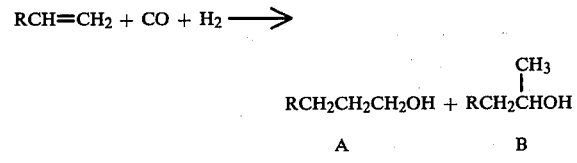

The amine promoters suitable for use in conjunction with a ruthenium compound in the desired hydroformylation reaction may take many different forms. Generally these promoters contain one or more tertiary substituted nitrogen atoms per molecule, with each trivalent nitrogen bonded to one or more carbon atoms. These amines may be aryl or aliphatic amines, or they may be n-heterocyclic amines; they may be diamines, containing two tertiary nitrogen donor atoms per molecule, polyamines or monoamines. The tertiary substituted nitrogen atoms in the diamine and polyamine structures may be separated by 0 to 12 carbon atoms, or they may be bonded to different cyclopentadienyl or arene groups of a metallocene.

Suitable tertiary amine promoters containing one or more n-heterocyclic ring structure include 2,2'-dipyridyl, pyridine, 1,10-phenanthroline, 3,5 lutidine, 2,6 lutidine, 2,2'-dipyridylamine, 2,3'-dipyridyl, 2,4'-dipyridyl, 2,2',2" terpyridyl, 2,4,6-tri(2-pyridyl)-s-triazine, 4,4' dipyridyl 4,4' dimethyl-2,2'-dipyridyl, 2,6-diphenylpyridine, diphenyl-2-pyridylmethane, 2,5-dimethylpyrazine, 2,6-dimethoxypyridine, 4-dimethylaminopyridine and isoquinoline.

Suitable aliphatic and aryl tertiary amine promoters include N,N,N',N'-tetramethylethylenediamine, trimethylamine, triethylamine, tri-n-butylamine, N,N'-dimethylpiperazine, N,N,N',N'-tetramethyl-o-phenylenediamine, 1,8-bis(dimethylamino) naphthalene, 1,2-dimethylpyrroline, 1,2-dipiperidinoethane, 1,4-diazabicyclo (2.2.2) octane, N,N,N',N' tetramethyl-1,3-propylenediamine, n-methylpyrrole, and hexamethylene tetramine.

The preferred tertiary amine promoters for the practice of this invention are bidentate n-heterocyclic compounds, such as 2,2'-dipyridyl.

The tertiary amine promoter, added in conjunction with the ruthenium-containing compound is, prior to its catalytic use in making alcohols and aldehydes, first dispersed in the low-melting quaternary phosphonium salt. It may be noted from the comparative Examples XLII-XLIV and XLV-XVIII that the addition of the tertiary amine promoter, e.g. 2,2'-dipyridyl, has the effect of:
(a)Increasing the linearity of the product alcohols (e.g. from 65% to 87% in Examples XLV and XLVII), and
(b)Lowering the amount of by-product alkane formed (c.f. Examples XLVII and XLV as well as Examples XLII and XLIV).

The olefins employed in the practice of this invention include internal and terminal olefins containing two to thirty carbon atoms and mixtures of the same. Examples of suitable olefins include straight-chain terminal olefins such as propylene, 1-butene, 1-octene, 1-decene, 1-dodecene, 1-tetradecene, and 1-hexadecene. Also suitable are branched-chain, terminal olefins such as 3-methyl-1-pentene, 4-methyl-1-hexene, 3,3-dimethyl-1-butene and 3,4-dimethyl-1-hexene. Linear and branched, internal olefins are also suitable substrates for this hydroformylation. Examples include 2-octene, 3-octene, 4-octene, mixed internal octenes, mixed internal decenes, mixed internal undecenes and dodecenes as well as 2-pentene, 3-hexene, 5-decene, 2-decene, 2-dodecene, and 5-methyl-2-hexene. Cyclic olefins like cyclohexene, cyclopentene, cycloheptene and their branched derivatives such as 1-methyl cyclohexene and 2-ethylcyclopentene are also useful in the practice of this invention.

Particularly preferred are straight-chain terminal olefins such as propylene, 1-butene, 1-octene, 1-decene and 1-dodecene, as well as linear internal olefins such as 2-octene, mixed internal octenes, mixed internal undecenes and mixed internal $C_{13}$-$C_{14}$ olefins, as well as terminal, internal olefin mixtures thereof.

Where oxonation is performed on linear alpha olefins, the corresponding OXO alcohols are prepared in good yield with linearity of the alcohol fraction reaching 93%. This selective oxonation reaction is demonstrated by Example I and illustrated by the following equation:

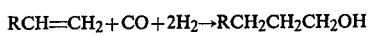

Where oxonation is performed on linear alpha olefins to yield primarily aldehyde products, the linearity of said aldehyde fraction may reach 98% when using the ruthenium-amine promoter catalyst systems of this invention. The selective oxonation reaction is demonstrated in Example II and illustrated by the following equation:

$$RCH_2=CH_2+CO+H_2 \rightarrow RCH_2CH_2CHO$$

The quantity of ruthenium catalyst employed in the instant invention is not critical and may vary over a wide range. In general, this improved process is desirably conducted in the presence of a catalytically effective quantity of the active ruthenium species, in conjunction with a tertiary amine promoter, and dispersed in a low-melting quaternary phosphonium salt which gives the desired products in reasonable yields. The reaction proceeds when employing as little as about $1 \times 10^{-6}$ weight percent, and even lesser amounts, of ruthenium together with about $1 \times 10^{-6}$, weight percent of an amine promoter and about $1 \times 10^{-6}$ weight percent of quaternary phosphonium salt basis the total weight of the reaction mixture. The upper concentration is dictated by a variety of factors including catalyst cost, partial pressures of carbon monoxide and hydrogen, operating temperature etc. A ruthenium catalyst concentration of from about $1 \times 10^{-5}$ to about 30 weight percent ruthenium in conjunction with an amine promoter concentration of from about $1 \times 10^{-5}$ to about 30 weight percent and a low-melting quaternary phosphonium salt concentration of from about 0.1 to about 80 weight percent based on the total weight of reaction mixture is generally desirable in the practice of this invention.

The temperature range which can usefully be employed in these syntheses is a variable dependent upon other experimental factors, including the pressure, the concentration and the choice of the particular species of ruthenium catalyst among other things. The range of operability is from about 50° to 350° C. when superatmospheric pressures of syngas are employed. A narrow range of 100°–220° C. represents the preferred temperature range.

Superatmospheric pressures of 100 psi or greater lead to substantial yields of alcohols by the process of this invention. A preferred operating range is from 500 psi to 3000 psi, although pressures above 3000 psi also provide useful yields of desired alcohol.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may or may not undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired oxonation reaction.

The major by-product of these alcohol/aldehyde syntheses are most commonly alkanes, isomerized alkenes and their aldol derivatives, which are, of course, also useful compounds and major articles of commerce. The alcohols and other products can easily be separated from one another by conventional means, e.g. fractional distillation in vacuo.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alcohol product, and said material may be recovered by methods well known in the art, such as distillation, fractionation, extraction and the like. A fraction rich in ruthenium catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

Having described the inventive process, the following examples are submitted to supply specific and illustrative embodiments:

EXAMPLE I

Ruthenium (IV) oxide (1.146 g, 6.0 mmole) plus 2,2'-dipyridyl (0.937 g, 6.0 mmole) was dispersed in tetra-n-butylphosphonium bromide (10.0 g, 29.5 mmole), diluted with 1-octene (22.4 g, 200 mmole) and transferred in a glass liner, under $N_2$ purge, to an 850 ml capacity pressure reactor equipped with heating and means of agitation. The reactor was sealed, flushed with $CO/H_2$ and pressured to 2000 psi, total pressure, with $CO/H_2(1:2)$. The mixture was heated to 160° C. with rocking, held at temperature for 4 hours and then allowed to cool.

Upon reaching ambient temperature, the reactor pressure (1600 psi) was noted, a typical gas sample taken, and the excess gas vented. The red liquid product (39.4 g) was analyzed by glc and Karl Fischer titration.

Analysis of a typical liquid sample showed the following composition:
- 17.6 wt. % octene
- 10.6 wt. % octane
- 28.2 wt. % linear nonanal
- 5.9 wt. % branched nonanals
- 26.6 wt. % linear nonanol
- 2.1 wt. % branched nonanols
- 3.0 wt. % water Estimated linearity of the nonanol fraction is 93%. Estimated conversion of the octene charge is 79%. Estimated yield of nonanals plus nonanols (basis octene converted) is 76 mole %.

EXAMPLE II

Ruthenium oxide (1.146 g, 6.00 mmole) plus 2,2'-dipyridyl (0.937 g, 6.0 mmole) was dispersed in tetra-n-butylphosphonium bromide (10.0 g, 29.5 mmole), diluted with 1-octene (22.4 g 200 mmole) and transferred in a glass liner, under $N_2$ purge, to an 850 ml capacity pressure reactor equipped with heating and means of agitation. The reactor was sealed, flushed with CO/H$_2$ (1:2). The mixture was heated to 100° C. with rocking, held at temperature for 4 hours and then allowed to cool.

Upon reaching ambient temperature, the reactor pressure (1175 psi) was noted, a typical gas sample taken, and the excess gas vented. The two-phase liquid product (35.3 g) was analyzed by glc and Karl Fischer titration.

Analysis of typical lighter (top phase) liquid product (29 ml) showed the following composition:
81.3 wt. % octene
18.4 wt. % linear nonanal
0.2 wt. % branched nonanals
0.1 wt. % linear nonanol
3.0 wt. % water Estimated linearity of the nonanal fraction in this product phase is 98.9%.

EXAMPLE III–XXIV

In these examples the equipment and procedures of Example I are used, the reactor charge in each case is ruthenium(IV) oxide, hydrate (6.0 mmole), 2,2'-dipyridyl (6.0 mmole), tetra-n-butylphosphonium bromide (10 g) and 1-octene (22.4 g, 200 mmole), however different operating temperatures, pressures and CO/H$_2$ mole ratios are used. The data are summarized in Table I.

It may be noted that:

(a)Aldehyde product linearity reaches 97.6% in Example III.

(b)Alcohol product linearity reaches 90% or better in Examples VIII, XIV, XV and XVIII.

(c)Total alcohol plus aldehyde yield (basis octene converted) is 85 mole % in Example III.

(d)A wide range of operating conditions may be employed with the ruthenium-amine catalysts of this invention.

TABLE I

OXO ALCOHOLS AND ALDEHYDES FROM TERMINAL OLEFINS[a]

| Example | Operating TEMP °C. | Initial Pressure (psi) | | | Liquid Yield (g) | Octene | Octane | Nonyl Aldehydes | | Product Composition % Nonyl Alcohols | | H$_2$O | Alcohol Linearity | Aldehyde Linearity |
| --- | --- | --- | --- | --- | --- | --- | --- | --- | --- | --- | --- | --- | --- | --- |
| | | H$_2$ | CO | Total | | | | Linear | Branched | Linear | Branched | | | |
| III | 120 | 800 | 400 | 1200 | 25.9 | 37.3 | 4.5 | 49.1 | 1.2 | 2.8 | | 5.1 | | 97.6 |
| IV | 140 | 800 | 400 | 1200 | 26.2 | 26.4 | 7.7 | 49.8 | 1.9 | 9.4 | 1.4 | 4.7 | 87 | 96 |
| V | 160 | 800 | 400 | 1200 | 27.1 | 16.7 | 8.6 | 21.8 | 5.1 | 34.2 | 4.0 | 3.2 | 90 | |
| VI | 180 | 800 | 400 | 1200 | 27.3 | 10.4 | 11.5 | 0.5 | 1.5 | 55.3 | 14.2 | 1.4 | 80 | |
| VII | 200 | 800 | 400 | 1200 | 28.1 | 1.0 | 15.5 | 0.1 | 0.5 | 48.8 | 25.9 | 1.1 | 65 | |
| VIII | 180 | 300 | 900 | 1200 | 25.5 | 10.8 | 7.5 | 11.3 | 4.8 | 42.5 | 4.4 | 0.8 | 91 | |
| IX | 180 | 400 | 800 | 1200 | 27.6 | 8.7 | 8.6 | 4.0 | 3.9 | 48.0 | 8.1 | 1.7 | 86 | |
| X | 180 | 600 | 600 | 1200 | 27.6 | 8.8 | 8.8 | 2.1 | 3.2 | 49.7 | 9.3 | 1.2 | 84 | |
| XI | 180 | 800 | 400 | 1200 | 27.3 | 10.4 | 11.5 | 0.5 | 1.5 | 55.3 | 14.2 | 1.4 | 80 | |
| XII | 180 | 900 | 300 | 1200 | 27.4 | 12.7 | 10.4 | 1.5 | 3.8 | 49.3 | 15.2 | 1.7 | 76 | |
| XIII | 160 | 400 | 200 | 600 | 26.9 | 22.1 | 11.2 | 1.1 | 1.9 | 41.6 | 14.9 | 1.3 | 74 | |
| XIV | 160 | 800 | 400 | 1200 | 27.1 | 16.7 | 8.6 | 21.8 | 5.1 | 34.2 | 4.0 | 3.2 | 90 | |
| XV | 160 | 1333 | 666 | 2000 | 27.3 | 17.6 | 10.6 | 28.2 | 5.9 | 26.6 | 2.1 | 3.0 | 93 | |
| XVI | 160 | 2000 | 1000 | 3000 | 27.4 | 17.1 | 10.0 | 30.1 | 6.2 | 22.5 | 2.8 | 6.2 | 89 | |
| XVII | 180 | 800 | 800 | 1600 | 28.2 | 8.3 | 7.8 | 10.0 | 5.3 | 43.5 | 5.5 | 1.9 | 89 | |
| XVIII | 180 | 800 | 1600 | 2400 | 28.2 | 9.8 | 6.7 | 23.4 | 7.6 | 29.5 | 3.3 | 2.9 | 90 | |
| XIX | 180 | 800 | 2400 | 3200 | 27.0 | 9.7 | 4.1 | 12.1 | 7.3 | 31.8 | 8.1 | 3.0 | 80 | |
| XX | 180 | 200 | 400 | 600 | 27.1 | 16.0 | 6.0 | 6.7 | 4.5 | 41.9 | 6.8 | 2.0 | 86 | |
| XXI | 180 | 400 | 400 | 800 | 25.6 | 15.8 | 8.7 | 4.1 | 2.7 | 46.5 | 6.5 | 2.1 | 88 | |
| XXII | 180 | 1200 | 400 | 1600 | 27.9 | 5.7 | 6.1 | 3.9 | 4.4 | 57.8 | 12.3 | 2.2 | 82 | |
| XXIII | 180 | 1600 | 400 | 2000 | 28.0 | 9.1 | 13.9 | 0.5 | 2.3 | 52.3 | 14.5 | 1.6 | 78 | |
| XXIV | 180 | 2000 | 400 | 2400 | 28.3 | 17.4 | 18.5 | 2.0 | 5.1 | 38.8 | 10.9 | 3.2 | 78 | |

[a]Experimental Series: Ru, 6.0 mmole; Bu$_4$PBr, 10.0 g; 1-octene, 200 mmole

Analysis of the brown-colored, heavier(bottom-phase) liquid product (13 ml) showed the following composition:
49.1 wt. % octene
1.9 wt. % octane
34.0 wt. % linear nonanals
0.4 wt. % branched nonanals
4.6 wt. % linear nonanols Estimated linearity of the nonanal fraction in this phase is 98.8%. Estimated total conversion of the octene charge is 27%. Estimated total yield of nonanols (basis octene change) is 77 mole %.

EXAMPLE XXV–XLI

In these Examples the equipment and procedures of Example I are used, the operating temperature (180° C.), initial pressure (1200 psi CO/H$_2$ (1:2)), and reaction time (4 hours) are held constant, however, different concentrations and mole ratios of reactants are employed. The data are summarized in Table II.

It may be noted that a wide range of ruthenium, 2,2'-dipyridyl, and 1-octene concentrations may be employed in the practice of this invention. Linearity of the product nonyl alcohols routinely exceeds 75% except in the absence of the 2,2'-dipyridyl promoter (Example XXX).

TABLE II

OXO ALCOHOLS AND ALDEHYDES FROM TERMINAL OLEFINS

| EXAMPLE | CATALYST PRECURSOR | OLEFIN FEED | LIQUID YIELD (g) | OCTENE | OCTANE | NONYL ALDEHYDES | | PRODUCT COMPOSITION (%) NONYL ALCOHOLS | | H2O | ALCOHOL LINEARITY (%) |
|---|---|---|---|---|---|---|---|---|---|---|---|
| | | | | | | LINEAR | BRANCHED | LINEAR | BRANCHED | | |
| XXV | ½(RuO$_2$-BIPY)[a] | 1-Octene | 26.1 | 21.2 | 13.7 | 18.3 | 12.3 | 19.3 | 4.0 | 4.7 | 83 |
| XXVI | ½(RuO$_2$-BIPY) | 1-Octene | 26.5 | 14.6 | 7.8 | 20.2 | 13.5 | 24.6 | 7.7 | 1.4 | 76 |
| XXVII | RuO$_2$-BIPY | 1-Octene | 26.9 | 15.4 | 7.9 | 14.8 | 10.2 | 31.0 | 9.1 | 1.5 | 77 |
| XXVIII | 2(RuO$_2$-BIPY) | 1-Octene | 27.1 | 16.8 | 9.2 | 5.9 | 6.9 | 40.8 | 13.2 | 2.1 | 76 |
| XXIX | 3(RuO$_2$-BIPY) | 1-Octene | 27.7 | 15.5 | 14.1 | 0.4 | 1.3 | 49.5 | 14.2 | 2.1 | 78 |
| XXX | RuO$_2$ | 1-Octene | 27.4 | — | 16.8 | 0.2 | 1.5 | 38.5 | 22.1 | 0.9 | 64 |
| XXXI | RuO$_2$-¼ BIPY | 1-Octene | 27.9 | 9.0 | 13.1 | 4.3 | 10.1 | 31.6 | 10.1 | 3.4 | 76 |
| XXXII | RuO$_2$-½ BIPY | 1-Octene | 26.2 | 10.0 | 16.9 | 11.3 | 11.2 | 28.9 | 7.5 | 2.3 | 79 |
| XXXIII | RuO$_2$-BIPY | 1-Octene | 26.9 | 15.4 | 7.9 | 14.8 | 10.2 | 31.0 | 9.1 | 1.5 | 77 |
| XXXIV | RuO$_2$-1¼ BIPY | 1-Octene | 29.9 | 13.8 | 13.9 | 8.1 | 7.9 | 37.7 | 7.0 | 2.0 | 84 |
| XXXV | RuO$_2$-2 BIPY | 1-Octene | 26.8 | 15.3 | 12.6 | 7.4 | 7.3 | 40.9 | 9.0 | 1.4 | 82 |
| XXXVI | RuO$_2$-3 BIPY | 1-Octene | 26.7 | 13.4 | 11.4 | 4.5 | 5.6 | 42.3 | 9.2 | 2.4 | 82 |
| XXXVII | RuO$_2$-BIPY[b] | ½[1-Octene] | 13.0 | 12.4 | 7.8 | 10.7 | 7.9 | 28.0 | 5.5 | 3.2 | 84 |
| XXXVIII | RuO$_2$-BIPY[b] | 1-Octene | 26.5 | 14.6 | 7.8 | 20.2 | 13.5 | 24.6 | 7.7 | 1.4 | 76 |
| XXXIX | RuO$_2$-BIPY[b] | 1½[1-Octene] | 39.8 | 18.7 | 13.5 | 17.9 | 13.7 | 20.4 | 3.9 | 2.8 | 81 |
| XL | RuO$_2$-BIPY[b] | 2[1-Octene] | 52.2 | 22.1 | 13.9 | 21.4 | 15.7 | 15.9 | 3.6 | 4.7 | 82 |
| XLI | RuO$_2$-BIPY[b] | 3[1-Octene] | 75.1 | 26.2 | 11.2 | 22.5 | 16.3 | 12.7 | 3.6 | 8.6 | 78 |

[a]Experimental Series Conditions; Ru, 3.0 mmole; Bu$_4$PBr, 5.0 g; 1-Octene, 200 mmole; 180° C.; 1200 psi CO/H$_2$ (1:2)
[b]Experimental Series Conditions: Ru 6.0 mmole; Bu$_4$PBr, 10.0 g; 1-Octene, 200 mmole; 180° C., 1200 psi CO/H$_2$ (1:2)

EXAMPLE XLII

Ruthenium (IV) oxide hydrate (1.146 g, 6.0 mmole) plus 2,2'-dipyridyl (0.937 g, 6.0 mmole) was dispersed in tetrabutylphosphonium bromide (20.0 g, 58.9 mmole), diluted with 1-decene (15.8 g, 100 mmole) and transferred in a glass liner, under N$_2$ purge, to an 850 ml capacity pressure reactor equipped with heating and means of agitation. The reactor was sealed, flushed with CO/H$_2$ and pressured to 1200 psi with CO/H$_2$ (1:2). The mixture was heated to 180° C. with rocking, held at temperature for four hours and then allowed to cool.

Upon reaching ambient temperature, the reactor pressure (1075 psi) was noted, a typical gas sample taken, and the excess gas vented. The red liquid product (41.2 g) was analyzed by glc and Karl Fischer titration.

Analysis of a typical liquid sample showed the following composition:
54.4 wt. % 1-undecanol
11.8 wt. % branched C-11 alcohols
3.8 wt. % C-11 aldehydes
1.5 wt. % water
9.6 wt. % decane
10.9 wt. % unreacted decenes Analysis of typical gas samples showed the presence of:
64 wt. % Hydrogen
31 wt. % Carbon monoxide
0.5 wt. % Carbon dioxide Estimated linearity of the undecanol fraction is 82%. Estimated conversion of the undecene charge is 87%. Estimated yield of undecanols (basis decene charge) is 73 mole %.

COMPARATIVE EXAMPLE XLIII

Following the procedure of Example 1, the same 850 ml capacity pressure reactor is charged with a mixture of ruthenium(IV) oxide, (15.8 g, 100 mmole), 2,2'-dipyridyl (6.0 mmole) and 1-decene (15.8 g, 100 mmole). There is no tetrabutylphosphonium bromide fraction added in this comparative example. The reactor is sealed, flushed with CO/H$_2$ and pressured to 1200 psi with CO/H$_2$ (1:2). The mixture is heated to 180° C. with rocking, held at temperature for 4 hours and then allowed to cool.

An analysis of the liquid product (18.2 g) by glc and Karl Fischer titration shows the presence of:
23.8% 1-undecanol
6.4% branched C$_{11}$-alcohols
0.1% C$_{11}$-aldehydes
0.3% water
10.9% decane
58.3% unreacted decenes Estimated linearity of the undecanol fraction is 79 %. Estimated conversion of the decene charge is 41%. Estimated yield of undecanols product (basis decene charged) 28 mole %.

It may be noted that in this comparative example, both the conversion of olefins to oxo products, and the yield of desired undecanols, was significantly lower in the absence of the quaternary phosphonium salt, tetrabutylphosphonium bromide, than in previous examples (e.g. Examples I and XLII) where the salt is present throughout the oxonation.

COMPARATIVE EXAMPLE XLIV

Following the procedures of Example XLII & XLIII, the same 850 ml capacity pressure reactor is charged with a mixture of ruthenium(IV) oxide, hydrate (6.0 mmole) and 1-decene (15.8 g, 100 mmole). There are no tetrabutylphosphonium bromide or 2,2'-dipyridyl fractions added in this comparative example. The reactor is sealed, flushed with CO/H$_2$ and pressured to 1200 psi with CO/H$_2$ (1:2). The mixture is heated to 180° C. with rocking, held at temperature for 4 hours and then allowed to cool.

An analysis of this liquid product (19.8 g) by glc and Karl Fischer titration shows the presence of:
36.7% 1-undecanol
23.9% branched C$_{11}$-alcohols
3.4% C$_{11}$-aldehydes
1.1% water
32.8% decane
0.2% unreacted decenes Estimated linearity of the undecanol fraction is 61%. Estimated yield of undecanols product (basis decene charged) is 61 mole %.

It may be noted that in this comparative example, both the yield of total undecanols, and the linearity to the desired 1-undecanol, is significantly lower in the absence of the quaternary phosphonium salt, tetrabutylphosphonium bromide, and N-heterocyclic promoter, 2,2'-dipyridyl, than in previous examples (e.g. Example XLII) where both the said salt and said promoter are present throughout the oxonation.

EXAMPLE XLV

A dispersion of ruthenium(IV) oxide, hydrate (6.0 mmole) plus 2,2'-dipyridyl (6.0 mmole) in tetrabutylphosphonium bromide (10.0 g, 29.5 mmole) is diluted with 11.2 g of 1-octene (100 mmole) and transferred in a glass-liner under $N_2$ purge, to an 850 ml capacity pressure reactor as described in Example 1. The reactor is sealed, flushed with $CO/H_2$ and pressured to 1200 psi with $CO/H_2$ (1:2). The mixture is heated to 180° C. with rocking, held at temperature for 4 hours and then allowed to cool.

An analysis of the liquid product (25.2 g) by glc and Karl Fischer titration shows the presence of:
  68.7% 1-nonanol
  8.6% 2-methyloctanol
  1.7% 2-ethylheptanol
  0.4% nonanals
  2.0% water
  9.1% octane
  9.0% unreacted octenes Estimated linearity of the nonanol fraction is 87%. Estimated conversion of the octene charge is 89%. Estimated yield of nonanols product (basis octene charged) is 72 mole %.

COMPARATIVE EXAMPLE XLVI

Following the procedures of Example XLV, the same 850 ml capacity pressure reactor is charged with a mixture of ruthenium(IV) oxide, hydrate (6.0 mmole), 2,2'-dipyridyl (6.0 mmole) and 1-octene (11.2 g, 100 mmole). There is *no* tetrabutylphosphonium bromide fraction added in this comparative example. The reactor is sealed, flushed with $CO/H_2$ and pressured to 1200 psi with $CO/H_2$ (1:2). The mixture is heated to 180° C. with rocking, held at temperature for 4 hours and then allowed to cool.

An analysis of the liquid product (14.1 g) by glc and Karl Fischer titration shows the presence of:
  37.4% 1-nonanol
  7.9% 2-methyloctanol
  0.2% 2-ethylheptanol
  0.1% nonanals
  4.0% water
  11.7% octane
  34.5% unreacted octenes Estimated linearity of the nonanol product fraction is 82%. Estimated conversion of the octene charge is 66%. Estimated yield of nonanols product (basis octene charged) is 38 mole %.

It may be noted that in this comparative example, the octene conversion and yield of desired nonanol products is significantly lower in the absence of the tetrabutylphosphonium bromide than in Example XLV where said salt is present throughout the oxonation.

COMPARATIVE EXAMPLE XLVII

The 850 ml capacity pressure reactor is charged with a mixture of ruthenium(IV) oxide, hydrate (6.0 mmole), tetrabutylphosphonium bromide (10.0 g, 29.5 mmole) and 1-octene (11.2 g, 100 mmole). There is *no* 2,2'-dipyridyl fraction added in this comparative example. The reactor is sealed, flushed with $CO/H_2$ and pressured to 1200 psi with $CO/H_2$ (1:2). The mixture is heated to 180° C. with rocking, held at temperature for 4 hours, and then allowed to cool.

An analysis of the liquid product (25.3 g) shows the presence of:
  50.7% 1-nonanol
  24.6% 2-methyloctanol
  3.1% 2-ethylheptanol
  0.1% nonanals
  0.5% water
  12.3% octane
  0.6% unreacted octenes Estimated linearity of the nonanol fraction is 65%. Estimated conversion of the octene charge is 99%. Estimated yield of nonanols product (basis octene charged) is 77 mole %.

It may be noted that in this comparative example the linearity to the desired 1-nonanol is significantly lower in the absence of the N-heterocyclic promoter, 2,2'-dipyridyl, than in examples where this promoter is present throughout the oxonation.

COMPARATIVE EXAMPLE XLVIII

Following the procedure of Example XLV, the 850 ml capacity pressure reactor is charged with a mixture of ruthenium (IV) oxide, hydrate (6.0 mmole) and 1-octene (11.2 g, 100 mmole). The reactor is sealed, flushed with $CO/H_2$, and pressured to 1200 psi with $CO/H_2$ (1:2). The mixture is heated to 180° C. with rocking, held at temperature for 4 hours and then allowed to cool.

An analysis of the product (13.0 g) shows the presence of:
  38.2% 1-nonanol
  15.8% 2-methyloctanol
  6.3% 2-ethylheptanol
  0.4% nonanals
  1.3% water
  33.5% octane
  1.8% octenes Estimated linearity of the nonanol fraction is 63%. Estimated yield of nonanols product (basis octene charged) is 50 mole %.

It may be noted that in this comparative example, both the yield of desired nonanol products and the linearity to 1-nonanol is significantly lower in the absence of the quaternary phosphonium salt, tetrabutylphosphonium bromide, and N-heterocyclic promoter, 2,2'-dipyridyl, than in Example XLV where both the said salt and said promoter are present throughout the oxonation.

EXAMPLE XLIX

Ruthenium (IV) oxide hydrate (1.146 g, 6.0 mmole) plus 2,2'-dipyridyl (0.937 g, 6.0 mmole) was dispersed in tetrabutylphosphonium bromide (20.0 g, 58.9 mmole) and was diluted with 16.8 g of 1-dodecene (100 mmole) and transferred in a glass liner, under $N_2$ purge, to an 850 ml capacity pressure reactor. The reactor was sealed, flushed with $CO/H_2$ and pressured to 1200 psi with CO/H$_2$ (1:2). The mixture was heated to 180° C. with rocking, held at temperature for 4 hours and then allowed to cool.

An analysis of the liquid product (41.8 g) by glc and Karl Fischer titration shows the presence of:
- 56.8% 1-tridecanol
- 13.4% branched C$_{13}$-alcohols
- 5.4% C$_{13}$-aldehydes
- 1.3% water
- 12.3% dodecane
- 9.9% unreacted dodecenes Estimated linearity of the tridecanol fraction is 81%. Estimated conversion of the dodecene charge is 88%. Estimated yield of tridecanols (basis dodecene charged) is 69 mole %.

EXAMPLES L–LX

In Table III, which follows, the same procedures are used as in previous examples, except a variety of tertiary amine promoters are used in conjunction with ruthenium(IV) oxide.

Generally, the most preferred amine promoters, basis the linearity and yields of desired alcohol product, are 2,2'-dipyridyl, 2,2'-dipyridyl amine (Example LVI) and N,N,N',N'-tetramethylethylenediamine (LV).

In Example LIX and LX in Table III different ruthenium precursors are used in conjunction with said amine promoters.

Estimated linearity of the nonanol fraction is 78%. Estimated yield of nonanols product (basis octene charged) is 61%.

EXAMPLE LXII

A dispersion of ruthenium(IV) oxide hydrate (6.0 mmole) plus 2,2'-dipyridyl (6.0 mmole) in tetrabutylphosphonium bromide (20.0 g, 58.9 mmole) is diluted with a mixed, internal C$_8$-olefin fraction (22.4 g, 200 mmole) and transferred in a glass-liner, under N$_2$ purge, to an 850 ml capacity pressure reactor equipped with heating and means of agitation. The reactor is sealed, flushed with CO/H$_2$ and pressured to 1200 psi with CO/H$_2$ (1:2). The mixture is heated to 180° C. with rocking, held at temperature for 4 hours and then allowed to cool.

Upon reaching ambient temperature, the reactor pressure (1000 psi) is noted, a typical gas sample taken, and the excess gas vented. The reddish-brown liquid product (47.1 g) is analyzed by glc and Karl Fischer titration.

Analysis of a typical liquid sample shows the following composition:
- 26.4% 1-nonanol
- 14.4% 2-methyl octanol
- 4.2% 1-nonanal
- 1.9% 2-methyl octanal
- 1.0% water

TABLE III

LINEAR OXO ALCOHOLS FROM α-OLEFINS[a]

| EXAMPLE | Ruthenium Catalyst | Promoter | Quaternary Salt | Octenes | Octane | Nonyl Aldehyde | Nonyl Alcohols Branched | Nonyl Alcohols Linear | Total Nonanols Yield (%) | Nonanol Linearity (%) |
|---|---|---|---|---|---|---|---|---|---|---|
| L | RuO$_2$×H$_2$O | DIPY[b] | Bu$_4$PBr | 10.4 | 11.5 | 2.0 | 13.7 | 55.3 | 61 | 80 |
| LI | " | 1,10-PHEN[b] | " | 4.2 | 11.4 | 2.0 | 18.9 | 55.7 | 74 | 75 |
| LII | " | PY[b] | " | 9.8 | 0.1 | 0.2 | 24.7 | 40.8 | 64 | 62 |
| LIII | " | 3,5-LUT[b] | " | 12.2 | 0.1 | 0.3 | 25.0 | 47.3 | 69 | 65 |
| LIV | " | 2,6-LUT[b] | " | 0.4 | 17.4 | 0.5 | 26.3 | 40.3 | 64 | 61 |
| LV | " | Me$_4$EDA[b] | " | 5.0 | 13.0 | 10.4 | 13.6 | 48.2 | 65 | 78 |
| LVI | " | DIPY-NH[b] | " | 9.7 | 8.4 | 19.3 | 7.1 | 42.5 | 56 | 84 |
| LVII | " | 2,3'-DIPY[b] | " | 0 | 16.4 | 1.8 | 22.1 | 47.9 | N.D.[c] | 68 |
| LVIII | " | 2,4'-DIPY[b] | " | 0 | 22.4 | 0.2 | 28.6 | 38.5 | N.D.[c] | 57 |
| LIX | Ru$_3$(CO)$_{12}$ | DIPY | " | 9.6 | 11.3 | 2.9 | 7.5 | 44.9 | 47 | 86 |
| LX | Ru(AcAc)$_3$ | DIPY | " | 9.3 | 12.0 | 0.4 | 16.8 | 43.5 | 56 | 72 |

[a]Reaction charge: Ru, 6.0 mmole; Ru/N ratio 1:2; Bu$_4$PBr, 10.0 g; 1-octene, 100 mmole.
Run conditions: 180° C.; 1200 psi CO/H$_2$ (1:2) initial pressure; 4 hours
[b]DIPY, 2,2'-dipyridyl; 1,10-PHEN, 1,10-phenanthroline; 3,5-LUT, 3,5-lutidine; 2,6-LUT, 2,6-lutidine; PY, Pyridine; Me$_4$EDa, N,N,N',N'—Tetramethylethylenediamine, DIPY-NH, 2,2'-Dipyridylamine; 2,3'-DIPY, 2,3'-dipyridyl; 2,4'-DIPY, 2,4'-dipyridyl.
[c]N.D., Not Determined.

EXAMPLE LXI

Following the procedures of Example I, the same 850 ml capacity pressure reactor is charged with a mixture of ruthenium oxide hydrated (1.146 g, 6.0 mmole) in conjunction with 2,2'-dipyridyl (0.937 g, 6.0 mmole), with a Ru/N ratio of 1:2. The mixture is dispersed in hexadecyltri-n-butylphosphonium bromide (10.0 g, 19.7 mmole) is sealed, flushed with CO/H$_2$ and pressured to 1200 psi with CO/H$_2$ (1:2). The mixture is heated to 180° C. with rocking, held at temperature for 4 hours and then allowed to cool.

An analysis of the liquid product (38.5 g) by glc and Karl Fischer titration shows the presence of:
- 9.3 wt. % octenes
- 10.5 wt. % octane
- 1.7 wt. % 2-Ethylheptanol
- 13.1 wt. % 2-Methyloctanol
- 52.2 wt. % Linear Nonanol
- 43.0% unreacted octenes Analysis of typical gas samples show the presence of:
- 55% hydrogen
- 38% carbon monoxide
- 4.0% carbon dioxide
- 3.2% methane Estimated linearity of the nonanol fraction is 65%. Estimated linearity of the nonanal fraction is 69%. Total C$_9$-alcohol+aldehyde yield (basis octene converted) is 79 mole %.

EXAMPLE LXIII

A dispersion of ruthenium(IV) oxide hydrate (1.5 mmole) and 2,2'-dipyridyl (0.5 mmole) in tetrabutylphosphonium bromide (15.0 mmole) is diluted with a mixed $C_{11}$ internal olefin fraction (30.8 g, 200 mmole) and transferred in a glass liner under nitrogen purge, to a 300 ml capacity pressure reactor equipped with heating and means of agitation. The reactor is sealed, flushed with $CO/H_2$ and pressured to 1200 psi with $CO/H_2$ (1:1). The mixture is heated to 180° C. with stirring, held at temperature for 4 hours and then allowed to cool.

Upon reaching ambient temperature, the reaction pressure (910 psi) is noted, a typical gas sample taken, and the excess gas removed. The red liquid product (34.0 g) is analyzed by glc.

Analysis of a typical liquid sample shows the following composition:
- 12.1% n-undecane
- 7.2% undecenes
- 5.0% branched $C_{12}$ aldehydes
- 2.1% 1-dodecanal
- 25.1% branched $C_{12}$ alcohols
- 32.6% 1-dodecanol Analysis of typical gas samples show the presence of:
- 51.1% hydrogen
- 32.6% carbon monoxide
- 9.4% carbon dioxide

EXAMPLE LXIV

A dispersion of triruthenium dodecacarbonyl (0.5 mmole) and 2,6-lutidine (1.5 mmole) in tetrabutylphosphonium acetate (15.0 mmole) is diluted with $C_{11}$ internal olefin (30.5 g, 200 mmole) and transferred in a glass liner under nitrogen purge, to a 550 ml capacity pressure reactor equipped with heating and means of agitation. The reactor is sealed, flushed with $CO/H_2$ and pressured to 1400 psi with $CO/H_2$ (1:1). The mixture is heated to 180° C. with rocking held at temperature for 18 hours and then allowed to cool.

Upon reaching ambient temperature, the reaction pressure (1275 psi) is noted, a typical gas sample taken, and the excess gas removed. The red liquid product (38.2 g) is analyzed by glc.

Analysis of a typical liquid sample shows the following composition:
- 1.7% n-undecane
- 73.2% undecenes
- 1.3% branched $C_{12}$ aldehydes
- 1.5% 1-dodecanal
- 5.4% branched $C_{12}$ alcohols
- 6.3% 1-dodecanol Analysis of typical gas samples show the presence of:
- 47.2% hydrogen
- 49.5% carbon monoxide
- 0.3% carbon dioxide

What is claimed is:

1. A process for preparing predominately linear alcohols and aldehydes from olefins which comprises the steps of contacting a terminal and/or internal olefin and synthesis gas with a catalyst system comprising a ruthenium-containing compound in conjunction with a promoter from the group consisting of aryl amines, aliphatic amines and n-heterocyclic amines containing one or more tertiary substituted nitrogen atoms per molecule, with each trivalent nitrogen bonded to one or more carbon atoms, dispersed in a low-melting quaternary phosphonium salt and heating resultant reaction mixture under a pressure of 100 psi or greater at a temperature of at least 50° C. until said alcohols and aldehydes are formed.

2. The process of claim 1 wherein said olefins contain from 2-30 carbon atoms.

3. The process of claim 2 wherein said olefins are straight-chain terminal olefins containing 8-15 carbon atoms.

4. The process of claim 2 wherein said olefins are internal olefins containing 8-15 carbon atoms.

5. The process of claim 3 wherein said olefins are selected from the group consisting of 1-octene, 1-decene, and 1-dodecene.

6. The process of claim 4 wherein said olefins are selected from the group consisting of 2-octene, mixed $C_8$-internal olefins, and mixed $C_{11}$-internal olefins.

7. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

8. The process of claim 7 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate and triruthenium dodecarbonyl.

9. The process of claim 8 wherein said ruthenium containing compound is selected from the group consisting of ruthenium(IV) oxide, triruthenium dodecacarbonyl and ruthenium(III) acetylacetonate.

10. The process of claim 9 wherein said ruthenium containing compound is ruthenium(IV) oxide.

11. The process of claim 1 wherein said quaternary salt has a melting point less than about 180° C.

12. The process of claim 1 wherein said quaternary salt is a tetraalkylphosphonium salt.

13. The process of claim 12 wherein said alkyl groups contain 1-20 carbon atoms.

14. The process of claim 13 wherein said tetraalkylphosphonium salt is a tetrabutylphosphonium salt.

15. The process of claim 14 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

16. The process of claim 1 wherein said quaternary phosphonium salt is a mixed alkyl phosphonium quaternary salt containing two or more different alkyl groups per molecule.

17. The process of claim 16 wherein said mixed alkyl phosphonium quaternary is hexadecyltri-n-butylphosphonium bromide.

18. The process of claim 17 wherein said n-heterocyclic amine promoter is chosen from the group consisting of:
2,2'-dipyridyl, 1,10-phenanthroline, 3,5-lutidene, 2,6-lutidene 2,2'-dipyridylamine, 2,3'-dipyridyl, and 2,4'-dipyridyl.

19. The process of claim 1 wherein said aliphatic tertiary amine is N,N,N',N'-tetramethylethelenediamine 20. The process of claim 1 wherein said tertiary amine promoter is 2,2'-dipyridyl.

21. The process of claim 1 wherein said pressure is from about 500 psi to about 3000 psi.

22. The process of claim 1 wherein the mixture is heated to a temperature of from 100° C. to about 220° C.

23. The process of claim 1 wherein the ratio of $CO:H_2$ in the synthesis gas mixture is from 20:1 to 1:20.

24. The process of claim 1 wherein said ruthenium precursor is ruthenium(IV) oxide, said tertiary amine promoter is 2,2'-dipyridyl, said phosphonium salt is tetra-n-butyl phosphonium bromide and said olefin is a straight chain, terminal alpha olefin.

* * * * *